United States Patent [19]

Ichikawa et al.

[11] 3,966,818

[45] June 29, 1976

[54] NOVEL PROCESS FOR PREPARATION OF 4-HYDROXY-2,4,6-TRIMETHYL-2,5-CYCLOHEXADIENE-1-ONE

[75] Inventors: Yataro Ichikawa; Yoshiyuki Yamanaka; Hideki Tsuruta, all of Iwakuni, Japan

[73] Assignee: Teijin Limited, Osaka, Japan

[22] Filed: Mar. 19, 1973

[21] Appl. No.: 342,500

[30] Foreign Application Priority Data
Mar. 25, 1972 Japan.............................. 47-30160
Mar. 30, 1972 Japan.............................. 47-31920

[52] U.S. Cl............................................. 260/586 P
[51] Int. Cl.$^2$........................................ C07C 45/16
[58] Field of Search ................... 260/396 N, 586 P

[56] References Cited
UNITED STATES PATENTS

| | | | |
|---|---|---|---|
| 3,213,114 | 10/1965 | Braxton et al. ................. | 260/396 R |
| 3,646,073 | 2/1972 | Wollensak ...................... | 260/396 R |
| 3,658,852 | 4/1972 | Schuster ......................... | 260/396 R |
| T903,007 | 10/1972 | Dietl et al. ...................... | 260/396 N |

*Primary Examiner*—Vivian Garner
*Attorney, Agent, or Firm*—Sherman & Shalloway

[57] ABSTRACT

A process for preparing 4-hydroxy-2,4,6-trimethyl-2,5-cyclohexadiene-1-one comprising reacting 2,4,6-trimethyl phenol with molecular oxygen or a molecular oxygen-containing gas. The product (also called mesitylquinol) is an intermediate useful as a raw material for the synthesis of a variety of industrial chemicals such as a drugs, dyestuffs, and pigments.

22 Claims, No Drawings

NOVEL PROCESS FOR PREPARATION OF 4-HYDROXY-2,4,6-TRIMETHYL-2,5-CYCLOHEXADIENE-1-ONE

This invention relates to a novel process for preparing 4-hydroxy-2,4,6-trimethyl-2,5-cyclohexadiene-1-one. More specifically, this invention relates to a process for preparing 4-hydroxy-2,4,6-trimethyl-2,5-cyclohexadiene-1-one (also called mesitylquinol) comprising reacting 2,4,6-trimethylphenol (also called mesitol) with molecular oxygen or a molecular oxygen-containing gas.

4-Hydroxy-2,4,6-trimethyl-2,5-cyclohexadiene-1-one, i.e., mesitylquinol, is a compound having the formula (1)

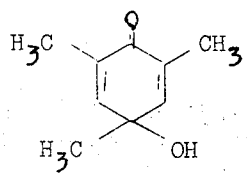

(1)

According to Ber. 33, 3639 (1900), this compound has been described as having a melting point of from 45.5° – 46°C., and according to the "Journal of Synthetic Organic Chemistry," Japan, Vol. 25, No. 3, 252–255 (1967), the same compound has been reported as having a melting point of 41°–43°C.

Mesitylquinol, when heated at 95°C. in the presence of an alkali such as NaOH, can be converted into 2,3,6-trimethylhydroquinone (TMHQ) represented by the formula (2).

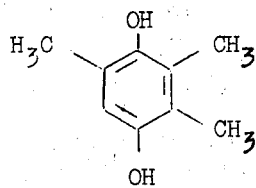

(2)

The so formed TMHQ can be used as an intermediate for the synthesis of vitamin E or directly as an industrial chemical such as an antioxidating agent or polymerization-inhibitors.

Therefore, the mesitylquinol prepared by the process of this invention is an intermediate useful as a raw material for the synthesis of a variety of industrial chemicals such as drugs, dyestuffs, and pigments, as mentioned above.

As processes for preparing the above-mentioned mesitylquinol, there can be cited, for example:

(A) A method in which 2,4,6-trimethylphenol represented by the formula (3)

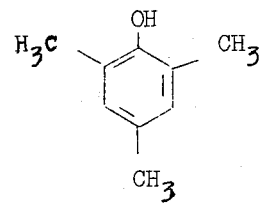

(3).

is suspended in an aqueous medium and is refluxed in the presence of Caro's acid ($H_2SO_5$) and magnesium carbonate to form mesitylquinol [see Ber. 36 2028 – 2041 (1903)], and (B) 2,4,6-trimethylnitrobenzene [formula (4)] is reduced with zinc powder to form N-(2,4,6-trimethyl)phenylhydroxyamine [formula (5)] which is then dislocated to turn itself into mesitylquinol [formula (1)], as represented by the reaction formulas (I)

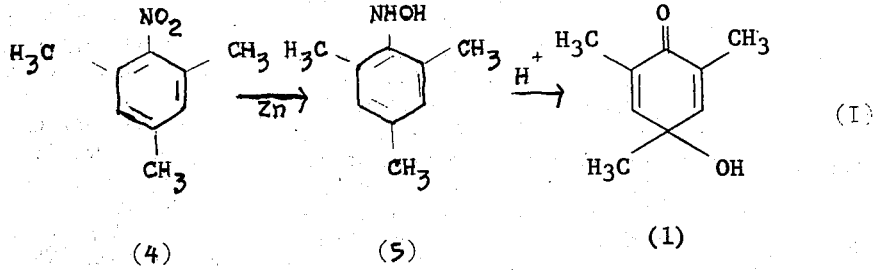

(I)

[see the "Journal of Synthetic Organic Chemistry", Japan, Vol. 25, No. 3, 252–255 (1967) mentioned above].

However, in method (A) above, not only is the Caro's acid ($H_2SO_5$) an expensive reagent, but also the yield of mesitylquinol is as small as several percent. According to method (B) above, methylene is nitrated to form 2,4,6-trimethylnitrobenzene of the formula (4), and the so formed 2,4,6-trimethylnitrobenzene is passed through the two steps as represented by the reaction formulas (I) above to form mesitylquinol. However, according to method (B), not only are three steps needed for the formation of mesitylquinol, but also the products have to be separated and purified during each step.

It is therefore an object of this invention to provide a novel one-step method for forming mesitylquinol from 2,4,6-trimethylphenol.

Another object of this invention is to provide a novel reaction for directly forming mesitylquinol by oxidizing 2,4,6-trimethylphenol with molecular oxygen or a molecular oxygen-containing gas.

Yet another object of this invention is to provide reaction conditions and a catalyst for forming mesitylquinol with high yields in one step by oxidizing 2,4,6-trimethylphenol with molecular oxygen.

Further objects and advantages of this invention will become clear as the description proceeds.

According to this invention, it was discovered that mesitylquinol can be formed by reacting 2,4,6-trimethylphenol with molecular oxygen or a molecular oxygen containing gas.

The reaction of this invention is represented by the following reaction formulas (II):

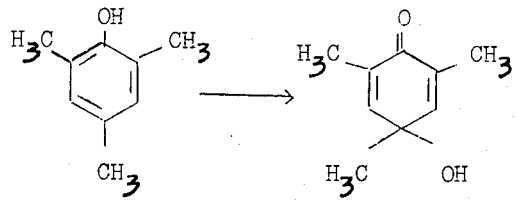

(II)

(3)                (1)

2,4,6-trimethylphenol    2,4,6-trimethyl-2,5-cyclohexadiene-1-one
(mesitol)               (mesitylquinol)

The invention is illustrated below in more detail. Also for convenience, the words "molecular oxygen or a molecular oxygen-containing gas" will appear simply as "molecular oxygen".

According to this invention, mesitylquinol is formed by the direct reaction of mesitol with molecular oxygen as represented by the above-shown reaction formula (II). The reaction represented by the reaction formula (II) can be effected either in the presence or absence of a liquid medium. For example, in the absence of a liquid medium, the mesitol may be reacted with molecular oxygen in the solid phase, or preferably in a molten state. The liquid medium may be any liquid which does not interrupt the reaction, an aqueous medium being preferred.

The molecular oxygen-containing gas may be of any mixture composed of molecular oxygen and an inert gas such as nitrogen, helium, argon, methane, or propane. In this invention the reaction can be effected appropriately by using pure oxygen or air. The molecular oxygen or molecular oxygen containing gas should preferably have a high partial pressure of molecular oxygen; the partial pressure of molecular oxygen may be as high as possible but not lower than 0.2 kg/cm$^2$. The reaction temperature may lie over any range if the reaction of the formula (II) proceeds and the resulted mesitylquinol is not decomposed or changed. Research conducted by the inventors of this application has proved that the temperatures ranging from as low as $-20°C$ to as high as $200°C$ allow the formation of the mesitylquinol.

As mentioned above, it is possible to carry out the reaction of this invention either in the presence or absence of a liquid medium. But the reaction should advantageously be carried out in the presence of the liquid medium. Such a liquid medium may be any liquid which does not interrupt the reaction of this invention, and the mesitol can be subjected to the reaction either in a melted or a suspended state.

Such a liquid medium may be any of:
i. water,
ii. an organic layer medium inert to the reaction of this invention, or
iii. a solution or a heterogeneous mixture of the organic liquid medium ii) above and water,
but should preferably be i) or iii).

As organic liquid media for use in ii) and iii) above, the following may be used:

I. Non-polar Liquid Media:
   a. Aliphatic hydrocarbons such as propane, propylene, butene, butylene, pentane, hexane, heptane, octane, nonane, decane, kerosene, ether, ligroine, kerosene, gasoline, kerosene paraffin,
   b. Alicyclic hydrocarbons such as cyclopentane, methylcyclopentane, cyclohexane, methylcyclohexane, ethylcyclohexane, dimethylcyclohexane, decalin, methyldecalin.
   c. Aromatic hydrocarbons such as benzene, toluene, xylene (ortho-, meta-, para- and their mixtures), ethylbenzene, cumene, trimethylbenzenes, tetralin, naphthalene, methylnaphthalenes,
   d. Symmetrically halogenated hydrocarbons such as carbon tetrachloride, II. Polar Liquid Media:
   e. water,
   f. alcohols such as methanol, ethanol, p-propanol, isopropanol, n-butanol, isobutanol, t-butanol, amyl alcohol, octanol,
   g. halogenated hydrocarbons such as chlorobenzene, dichlorobenzene, methylenedichloride, ethylenedichloride,
   h. ketones such as acetone, methyl ethyl ketone, methyl isobutyl ketone,
   i. ethers such as diethyl ether, tetrahydrofuran, dioxane,
   j. ester such as methyl acetate, ethyl acetate, propiolactone, methylbenzoate,
   k. sulfur-containing compounds, e.g., thioethers such as diethyl thioether; sulfones such as dimethyl sulfone; tetramethyl sulfone, sulfoxides such as dimethyl sulfoxide,
   l. amines such as trimethyl amine, pyridine, pyrrolidone,
   m. nitro compounds such as nitrobenzene, dinitrobenzene, 2,4-dinitrotoluene,
   n. cyano compounds such as acetonitrile, propionitrile, phthalonitrile, benzonitrile,
   o. amides such as dimethyl formamide (DMF), dimethyl acetamide (DMAC), tetramethylurea (TMU), hexamethyl phosphoryl amide (HMPA), N-methyl pyrrolidone (NMP), dimethyl formamide.

To obtain the aqueous solution of an organic liquid medium contained in (iii) above, only those which can be blended with water may be selected out of said organic liquid media. Also in this invention the reaction can be carried out by using a heterogeneously mixed liquid medium composed of water and those selected from the above-mentioned organic liquid media which will not be blended with water.

In this invention it is preferred to bring the mesitol into contact with molecular oxygen in water or in the abovementioned water-containing organic liquid medium under the oxygen partial pressure of at least 0.1 kg/cm$^2$ at a temperature of $-20°$ to $200°C$., preferably at a temperature of $0°$ to $150°C$.

According to this invention, in general, the higher the oxygen partial pressure, the more it is advantageous. And according to the research conducted by the inventors of this invention, it has been proved that within the oxygen partial pressure range of 0.1 kg/cm$^2$ to 50 kg/cm$^2$, the conversion of mesitol increases with the increase of the oxygen partial pressure; in a region where the reaction temperature is below $30°C$., especially below $20°C$., the conversion of mesitol increases with the increase of the reaction temperature, and in a region where the reaction temperature is above $100°C$., especially above $120°C$., the selectivity of the final product mesitylquinol tends to decrease.

Accordingly, the partial pressure of oxygen should be at least 5 kg/cm$^2$, especially at least 20 kg/cm$^2$, and its upper limit may be determined to include possible maximum range allowed by the reaction apparatus and operation of the reaction. The range of reaction temperature should preferably be from $0°$ to $120°C$., and specifically from $20°$ to $100°C$.

Also, the reaction time depends mainly on the reaction temperature; where the reaction temperature is low, the reaction time may be long, and where the reaction temperature is high, the reaction time may be short. The reaction time may be selected appropriately, from several seconds up to a few days (about 100 hours). Where the reaction temperature and other conditions are suitable, the reaction time of several seconds to several hours (e.g., 10 sec. to 5 hr.) allows the formation of the aimed mesitylquinol maintaining high conversion and selectivity.

The process of this invention when being performed in a system of a pH of above 5, should advantageously be conducted under non-acidic conditions. Hence, where the process of this invention is carried out in a water-containing liquid medium, the pH of said medium should be at least 5 and preferably at least about 6. Where the process of this invention is carried out in an organic liquid medium, it is recommended to use a neutral or basic organic liquid medium.

If the mesitol is reacted with molecular oxygen in accordance with this invention, part of the mesitol or oxidized product is oxidized and decomposed resulting in the formation of complicated acidic substances as by-products. It was observed that the reaction system shifts toward the acidic side as the conversion reaction of mesitol proceeds.

Therefore, where the process of this invention is being put into practice, it is advantageous to keep the reaction system at the time of initiating the reaction at a pH of at least 5 or more, especially at the non-acidic side, and preferably to acquire neutral to basic (or alkaline) state, as well as to keep the reaction system at the non-acidic side as long time as possible until the reaction is finished. Especially, the mesitylquinol can be formed maintaining good selectivity if the reaction system of this invention is maintained in a basic condition (alkaline condition) of as strong as a pH of at least 10, especially above 11.

In this way, in this invention it is preferred to react the mesitol with molecular oxygen in the presence of a buffer or a basic reagent.

The buffers may be conventional ones; e.g., alkali dihydrogenphosphates such as potassium dihydrogenphosphate; dialkali hydrogenphosphates such as disodium hydrogenphosphate; alkali salts of organic carboxylic acids such as borax, citric acid, lactic acid, or tartaric acid; tris(oxymethyl)aminomethane; 2,4,6-collidine; or combinations thereof.

In fact, in this invention, the final product mesitylquinol can be formed maintaining a selectivity as high as more than 70 % by conducting the reaction thereby adjusting the pH value of the reaction mixture at 7–8 based on the combination of the above-mentioned alkali dihydrogenphosphate and dialkali hydrogenphosphate.

Furthermore, 2,4,6-trimethylphenol (mesitol) used as a starting raw material may be one obtained by any conventional method and may contain other substances which will not interrupt the reaction. In addition, 2,4,6-trimethylphenolate obtained by reacting 2,4,6-trimethylphenol with a basic reagent may be used as a starting raw material, and in this case, the basic reagent does not necessarily have to be made present to perform the reaction.

Basic reagents for use in this invention should preferably be capable of forming the 2,4,6-trimethylphenoxy anion especially in the reaction system, and examples are alkali metals, alkaline earth metals, metals such as thallium and its compounds, or nitrogen-containing basic compounds.

The above-mentioned basic reagent of metals may be used in the form of a metal alone, hydride, oxide, hydroxide, carbonate, bicarbonate, alcoholate, phenolate, amide, organic metal compound, or complex compound. Of these, alkali metals and alkali earth metals, specifically alkali metals and their compounds are most suited.

Illustrating in detail, the alcohols and phenols for forming the above-mentioned alcoholate and phenolate may be of aliphatic, alicyclic, heterocyclic, or aromatic alcohols or phenols, and may have substituents acquiring a valency of 1 or 2 or more.

Organic metal compounds and complex compounds used in this invention should preferably be capable of forming 2,4,6-trimethylphenolate being reacted with 2,4,6-trimethylphenol. Such examples may be the reaction products of acetylated alkali, sodium naphthalate, triphenylmethane, and alkali metals; reaction products of cyclic glymes which are often called glyme crown compounds and alkali metals; hydrides such as NaH and KH; metal amides such as NaNH$_2$ and KNH$_2$.

Especially preferred examples of basic reagents are (1) potassium, sodium, (2) potassium hydroxide, sodium hydroxide, sodium carbonate, potassium carbonate, sodium bicarbonate, potassium bicarbonate; (3) alcoholates such as methylate, ethyl alcoholate, n-propyl alcoholate, isopropyl alcoholate, n-butyl alcoholate, iso-butyl alcoholate, t-butyl alcoholate, n-amyl alcoholate, hexyl alcoholate, 2-ethyl hexyl alcoholate and dodecyl alcoholate of potassium or sodium; (4) phenolates such as potassium-2,4,6-trimethylphenolate, and sodium-2,4,6-trimethylphenolate; and (5) hydroxides, oxides, or carbonates of beryllium, calcium, or magnesium, or alcoholates thereof.

These alcoholates and phenolates are used not only in their inherent solid form (purely crystalline or powdery form) but also in the form of a solution synthesized by a conventional method.

Where the reaction of this invention is being put into practice in the presence of the above-mentioned basic reagents, it is advantageous to use a solvent together with an organic liquid medium or its aqueous solution which is capable of dissolving such basic reagents.

Such basic reagent should in general be used in amounts, with respect to 1 mol of the starting material, of 0.0001 to 100 mol, preferably 0.001 to 10 mol, and most preferably in amounts of 0.01 to 5 mol. And where the reaction system is water, the basic reagents should be used in amounts sufficient to maintain the pH of the reaction system to be at least neutral, and especially in a strongly basic condition having a pH of at least 10.

When a 2,4,6-trimethylphenolate of alkali metals or alkaline earth metals is used as a starting material, the reaction system will contain a sufficient amount of basic reagent, and hence no additional basic reagents will necessarily have to be added. Of course, the use of such phenolates as starting materials should be contained in the scope of this invention.

Also, in this invention, a liquid organic basic material such as ammonia, dimethylformamide (DMF), dimethylacetamide (DMAC), N-methylpyrrolidone (NMP), hexamethylphosphoramide (HMPA), or tetramethylurea (TMU), may be used alone or in combination with the above-mentioned non-polar organic medium, for the purpose of conducting the process of this invention under a neutral to basic condition.

Furthermore, basic and, especially, strongly basic organic material such as guanidine, alkylguanidines, or DBU(1,8-diaza-bicyclo(5,4,0)undecen-7) may be added so that the reaction system is maintained at neutral to basic condition.

The process of this invention can be effected suitably even in the absence of the catalyst mentioned above. But where a catalyst is used, as a preferred embodiment of this invention, the catalyst should preferably be a metal of the group 1B or the group 8 of Periodic Table, or the compounds thereof. Platinum group metals such as palladium, platinum, and cobalt compounds, and especially certain cobalt complexes are suited. Also, for example, methylenic ketones such as methyl ethyl ketone, which produce radicals in the reaction system, are useful for the reaction of this invention. Where such catalysts are used, the reaction system does not necessarily have to be maintained basic (or alkaline), but it is advantageous to maintain the reaction system neutral or basic, especially strongly basic (or alkaline).

As the cobalt complexes, a compound of the formula (6)

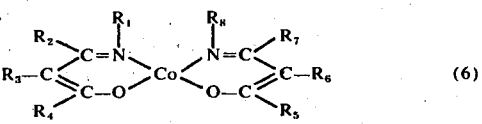

wherein $R_1$–$R_8$ may be the same or different and represent hydrogen or organic residues, or preferably of the formula (7)

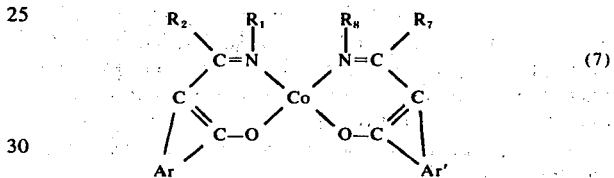

wherein $R_1$, $R_2$, $R_7$, and $R_8$ represent hydrogen or organic residues, and Ar and Ar' represent the groups which together with carbon form aromatic nuclei, can be used.

Of the cobalt complexes encompassed by the formula (7) above, cobalt-bis(salicylaldehyde)diimino complexes represented by the formulas (7a), (7b), and (7c) are preferable:

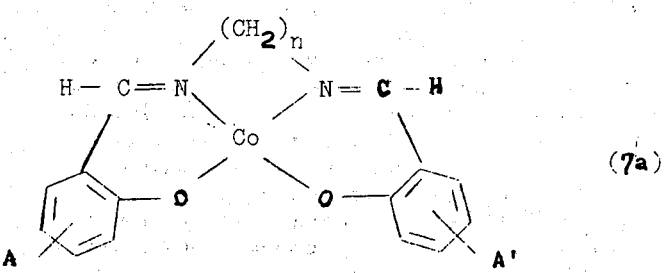

wherein, $n$ is an integer of 2–10, A and A' are hydrogen or substituents such as —$NO_2$, fluoro, —$OC_2H_5$,

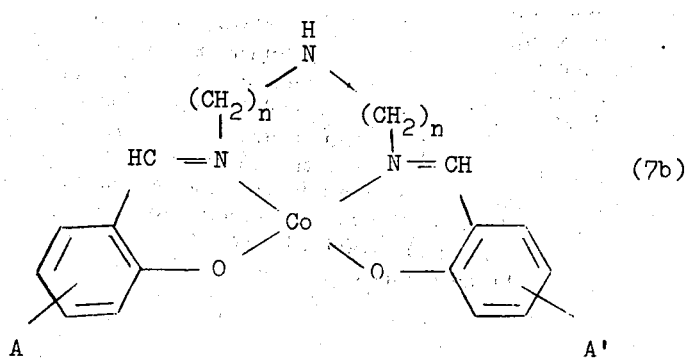

wherein n, A, and A' are as defined above, and

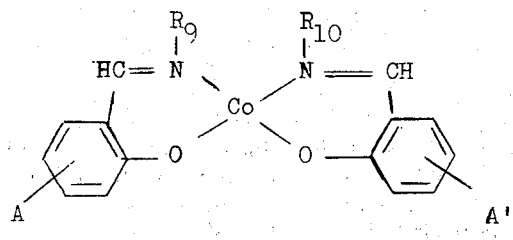

(7c)

wherein, $R_9$ and $R_{10}$ are hydrogen, phenyl, substituted phenyl, alkyl, —OH, hydroxyalkyl, or benzyl, A and A' are as defined above.

Moreover, cobalt-bis(O-oxyacetophenone)diimino complexes or the above-mentioned cobalt complexes on which has been coordinated a nitrogen-containing ligand such as pyridine or on which has been coordinated, are effective for the reaction of this invention, and should be encompassed by the scope of this invention.

Furthermore, β-diketo complexes of cobalt as cobalt complexes can be used as preferable catalysts. Preferable examples of such β-diketo complexes may be the cobalt complex having as ligand, cobalt and β-diketo group of the keto type and/or enol type represented by either one of the following formula (8) or (8')

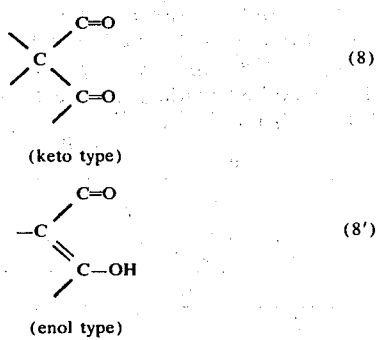

As such cobalt complexes, there may be cited β-diketone complexes of cobalt, β-ketoester complexes of cobalt, etc. The β-diketo complexes of cobalt are prepared by reacting cobalt compounds capable of forming β-diketo complexes, such as organic carboxylates of cobalt or a nitrate, perchlorate, chloride, oxide, or hydroxide of cobalt, with β-diketo group-containing compounds such as β-diketone, β-diketoester or salts of these (salts of an alkali metal such as sodium and potassium) which will be described hereinafter.

Examples of β-diketone include, for instance, acetylacetone, propionylacetone, butylacetone, isobutyrylacetone, caproylacetone, o-methylacetylacetone, tetraacetylethane, benzoylacetone, dibenzoylmethane, trifluoroacetylacetone, hexafluoroacetylacetone, benzoyltrifluoroacetone, and β-naphthoyltrifluoroacetone. The β-keto esters include, for instance, acetoacetic acid ester, and trifluoroacetoacetic acid ester.

Where the above-mentioned cobalt complexes are used as catalysts, the reaction of this invention should advantageously be carried out in an organic liquid medium.

Also in this invention, in addition to such cobalt complexes, suitable metals selected from the group 1B and the group 8 of Periodic Table or compounds thereof can be used as catalysts, as mentioned earlier.

Such catalysts may be of homogeneous ones which can dissolve in the reaction mixture of this inventon or may be of heterogeneous ones which do not dissolve in the reaction mixture.

For example, neglecting here whether the above-mentioned basic substances can be called catalysts or not, a fine powdery mixture of the raw material mesitol and caustic soda or an intimate mixture of the molten mesitol and powdery caustic soda being heated, in the former case, at about 30°C. and heated, in the latter case, at about 80°C., as well as being contacted with molecular oxygen, allows the formation of mesitylquinol maintaining the selectivity of about 30–60%.

As mentioned above, the process of this invention can be conducted in the absence of the liquid medium, but should in general be conducted in the liquid phase by using the liquid medium to advantage. Where the liquid medium is being used, the liquid medium should preferably be used in amounts, with respect to 1 part by weight of the raw material mesitol, of 0.1–100 parts by weight, especially 0.5–50 parts by weight, and most suitably 1–10 parts by weight.

Molecular oxygen used in this invention may be in any form if it contains molecular oxygen; substantially pure oxygen, air having high oxygen concentration being added with molecular oxygen, ordinary air, or a gas containing molecular oxygen being diluted with a gas inactive to the reaction such as nitrogen, helium, argon, or methane, are used usually.

The temperature for putting the process of this invention into practice may in general lie over the range of —20° to 200°C. With the temperature too low, the conversion of mesitol tends to be reduced and the selectivity of mesitylquinol also tends to be decreased. With the temperature too high, increased conversion will be allowed but the selectivity tends to be decreased. Accordingly, temperatures in a range of —10° to 150°C., especially 0° to 120°C., and more suitably 20° to 100°C. are desired for forming the mesitylquinol maintaining good conversion and selectivity.

As illustrated already with regard to the reaction pressure, the higher the molecular oxygen partial pressure, the more it is desirable. But due to the apparatus and operational convenience, good results can be obtained with the pressure of, generally, less than 1000 kg/cm², especially less than 500 kg/cm², and more specifically less than 300 kg/cm². The pressure may be reduced, normal, or elevated; and the partial pressure of molecular oxygen should preferably be at least 0.1 kg/cm², and especially at least 0.2 kg/cm². The optimum pressure of molecular oxygen should, in terms of its partial pressure, be at least 40 kg/cm².

The process of this invention can be carried out either in a continuous method or batch method. Also the method of bringing the reaction mixture which will be reacted into contact with molecular oxygen may be any method used in conventional gas-liquid catalytic reaction; for example, a stirring vessel (gas blowing type or gas introducing type), forming tower, packing tower, plate tower, countercurrent continuous gas-liquid contacting method, or parallel flow continuous gas-liquid contacting method.

As mentioned in the foregoing, according to the process of this invention, 2,4,6-trimethyl-2,5-cyclohexanediene-1-one (mesitylquinol) of the formula (1)

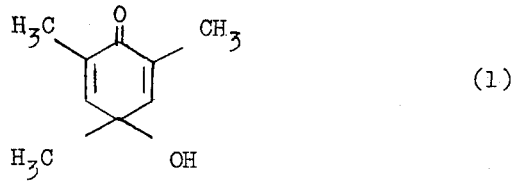

(1)

is obtainable.

The separation of mesitylquinol from the oxidized reaction mixture obtained through the process of this invention can be performed in a conventional manner, for example, by neutralizing the reaction mixture as required, filtering the crude mesitylquinol, purifying the filtered mesitylquinol by using an appropriate organic solvent such as kerosene ether, and recrystallizing the resulting mesitylquinol in water as required.

The mesitylquinol obtained by the process of this invention in its crude form or after being purified can be converted through the dislocation reaction into 2,3,6-trimethylhydroquinone.

EXAMPLES 1–2

2 Parts of 2,4,6-trimethylphenol and the solvents shown in Table 1 below were fed to the stainless steel autoclave equipped with a gas-introducing port, temperature recorder, and stirrer, and were reacted under the conditions shown in Table 1, in the absence of catalyst. Recovery and analyses of the reaction products showed the results as listed in Table 1.

Table 1

| | Reaction pressure | Solvent | Temp. (°C.) | Time (hour) | Unreacted starting material (parts) | Conversion | Object product (part) | Selectivity |
|---|---|---|---|---|---|---|---|---|
| Example 1 | Oxygen 100 Kg/cm²G | water | 80 | 6 | 0.202 | 89.9 | 0.022 | 1.1 |
| Example 2 | Air 130 Kg/cm²G | Water: MeOH 1:1* | 80 | 2 | 1.666 | 16.7 | 0.002 | 0.5 |

*:weight ratio

EXAMPLE 3

2 Parts of 2,4,6-trimethylphenol were fed to a stainless steel autoclave equipped with a gas-introducing port and temperature recorder and were reacted at a temperature and for a period of time as shown in Table 2 below under an oxygen pressure of 100 Kg/cm²G. The reaction product recovered showed results as listed in Table 2.

Table 2

| | Catalyst (part) | Temp. (°C.) | Time (hour) | Unreacted starting material (parts) | Conversion (%) | Object product (parts) | Selectivity (%) |
|---|---|---|---|---|---|---|---|
| Example 3 | — | 80 | 6 | 1.297 | 35.2 | 0.013 | 1.7 |

EXAMPLES 4–7

2 Parts of 2,4,6-trimethylphenol and 100 parts of the buffer solution of the composition prepared from the compounds listed in Table 3 below were fed to a stainless steel autoclave equipped with a gas-introducing port, temperature recorder, and stirrer, and were reacted under the conditions as shown in Table 3, under an oxygen pressure of 100 Kg/cm²G. Recovery and analyses of the reaction product showed results as shown in Table 3.

Table 3

| | Buffer solution composition (parts)* | | pH | Temp. (°C.) | Time (hour) | Unreacted starting material (parts) | Conversion (%) | Object product (parts) | Selectivity (%) |
|---|---|---|---|---|---|---|---|---|---|
| Example 4 | Acidic potassium phthalate | 14 | 5 | 80 | 2 | 1.871 | 6.5 | 0.001 | 0.3 |
| | NaHCO₃ | 2.7 | | | | | | | |
| Example 5 | KH₂PO₄ | 23.2 | 6 | 80 | 2 | 1.243 | 37.9 | 0.006 | 0.71 |
| | Na₂HPO₄ | 4.3 | | | | | | | |
| Example 6 | KH₂PO₄ | 9.1 | 7 | 30 | 2 | 1.330 | 33.5 | 0.587 | 78.2 |
| | Na₂HPO₄ | 18.9 | | | | | | | |

Table 3-continued

| | Buffer solution composition (parts)* | pH | Temp. (°C.) | Time (hour) | Unreacted starting material (parts) | Conversion (%) | Object product (parts) | Selectivity (%) |
|---|---|---|---|---|---|---|---|---|
| Example 7 | H$_3$BO$_3$<br>Na$_2$B$_4$O$_7$.10H$_2$O | 11.8<br>9.1 | 8 | 80 | 2 | 1.087 | 45.7 | 0.172 | 16.8 |

*:Parts of a buffer in 1000 parts of water.

EXAMPLES 8–14

2 Parts of 2,4,6-trimethylphenol in aqueous solution having pH values shown in Table 4 below, and prepared from the compounds shown below, were fed to a stainless steel autoclave equipped with a gas-introducing port, temperature recorder and stirrer, and were reacted under an oxygen pressure of 100 Kg/cm$^2$G at a temperature of 80°C. for 120 minutes with violent stirring. Recovery and analyses of the reaction products showed the results as listed in Table 4.

Table 4

| | pH-adjusting agent | pH | Unreacted starting material (parts) | Conversion (%) | Object product (parts) | Selectivity (%) |
|---|---|---|---|---|---|---|
| Example 8 | NaHCO$_3$ | 7 | 1.693 | 15.4 | 0.012 | 3.5 |
| Example 9 | NaHCO$_3$ | 8 | 1.830 | 8.5 | 0.006 | 3.2 |
| Example 10 | Na$_2$CO$_3$ | 7 | 1.328 | 3.6 | 0.005 | 0.7 |
| Example 11 | Na$_2$CO$_3$ | 8 | 1.669 | 16.6 | 0.005 | 1.3 |
| Example 12 | Na$_2$CO$_3$ | 12 | 0.041 | 97.9 | 0.754 | 34.4 |
| Example 13 | NH$_4$OH | 10 | 1.578 | 21.1 | 0.001 | 0.1 |
| Example 14 | NH$_4$OH | 12 | 0.007 | 99.7 | 0.635 | 28.5 |

EXAMPLES 16–18

2 Parts of 2,4,6-trimethylphenol, alkaline earth metal hydroxide as listed in Table 6 below, and 100 parts of water were fed to a stainless steel autoclave equipped with a gas-introducing port, temperature recorder and stirrer, and were reacted under an oxygen pressure of 100 Kg/cm$^2$G, and at a temperature of 80°C., for 120 minutes with violent stirring. Recovery and analyses of the reaction mixture showed the results as listed in Table 6.

Table 6

| | Alkaline earth material hydroxide (parts) | Unreacted starting material (parts) | Conversion (%) | Object product (parts) | Selectivity (%) |
|---|---|---|---|---|---|
| Example 16 | Mg(OH)$_2$ (0.058) | 1.028 | 48.5 | 0.071 | 6.5 |
| Example 17 | Ca(OH)$_2$ (0.074) | 0.950 | 52.5 | 0.465 | 39.5 |
| Example 18 | Ba(OH)$_2$.8H$_2$O (0.315) | 0.825 | 58.8 | 0.429 | 32.6 |

EXAMPLE 15

2 Parts of 2,4,6-trimethylphenol and 0.9 parts of caustic soda (NaOH) were fed to a stainless steel autoclave equipped with a gas-introducing port and temperature recorder, under an oxygen pressure of 100 Kg/cm$^2$G. The reaction was carried out at a temperature and for a period of time as shown below in Table 5. Recovery and analyses of the reaction product showed the results as listed in Table 5.

EXAMPLES 19–21

2 Parts of 2,4,6-trimethylphenol, cobalt complexes as shown in Table 7 below, and 50 parts of benzene, were fed to a stainless steel autoclave equipped with a gas-introducing port, temperature recorder and stirrer, and were reacted under an air pressure of 120 Kg/cm$^2$G, and at a temperature of 30°C., for 120 minutes with violent stirring. Recovery and analyses of the reaction products showed the results as listed in Table 7.

Table 5

| | Temp. (°C.) | Time (hour) | Unreacted starting material (parts) | Conversion (%) | Object product (parts) | Selectivity (%) |
|---|---|---|---|---|---|---|
| Example 15 | 30 | 6 | 1.59 | 20.5 | 0.233 | 50.7 |

Table 7

| | Cobalt complex (parts) | Unreacted starting material (parts) | Conversion (%) | Object product (parts) | Selectivity (%) |
|---|---|---|---|---|---|
| Example 19 | Cobalt-di(salycylal) ethylenediimine-pyridine (0.404) | 0.050 | 97.5 | 0.188 | 8.7 |
| Example 20 | Cobalt-phthalocyanine (0.572) | 1.890 | 5.5 | 0.009 | 7.3 |
| Example 21 | Cobalt-acetylacetone (0.257) | 1.608 | 19.6 | 0.117 | 26.6 |

Table 9

| | Catalyst (parts) | Reaction pressure | Temp. (°C.) | Time (hour) | Unreacted starting material (parts) | Conversion (%) | Object product (parts) | Selectivity (%) | Note |
|---|---|---|---|---|---|---|---|---|---|
| Example 24 | methyl ethyl ketone (0.072) | Air 119 Kg/cm²G | 80 | 2 | 0.501 | 75 | 0.586 | 35 | |
| Example 25 | Pd/C/NaOH (0.1) (0.7) | Air 120 Kg/cm²G | 30 | 2 | 0.303 | 77.7 | 0.309 | 26.1 | Raw material 1.36 parts |
| Example 26 | TlOH (0.221) | Oxygen 100 Kg/cm²G | 80 | 2 | 0.129 | 93.6 | 0.096 | 4.6 | |

EXAMPLES 22–23

2 Parts of 2,4,6-trimethylphenol, organic bases as shown in Table 8 below, and 100 parts of water were fed to a stainless steel autoclave equipped with a gas-introducing port, temperature recorder, and stirrer, and were reacted under the conditions as listed in Table 8. Recovery and analyses of the reaction product showed the results as listed in Table 8.

Table 8

| | Organic base (parts) | Reaction pressure | Temp. (°C.) | Time (hour) | Unreacted starting material (parts) | Conversion (%) | Object product (parts) | Selectivity (%) |
|---|---|---|---|---|---|---|---|---|
| Example 22 | NH=C(NH₂)₂ (0.60) | Oxygen 100 Kg/cm²G | 30 | 2 | 1.390 | 30.5 | 0.200 | 29.3 |
| Example 23 | 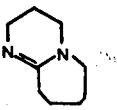 (0.152) | Air 120 Kg/cm²G | 80 | 2 | 1.272 | 36.4 | 0.077 | 9.5 |

EXAMPLES 24–26

2 Parts of 2,4,6-trimethylphenol, catalysts as shown in Table 9 below, and solvents were fed to a stainless steel autoclave equipped with a gas-introducing port, temperature recorder and stirrer, and were reacted under the conditions as listed in Table 9. Recovery and analyses of the reaction products showed the results as listed in Table 9.

EXAMPLES 27–30

1.36 Parts of 2,4,6-trimethylphenol, alkali metal hydroxides as listed in Table 10 below, and 25 parts of water were fed to an autoclave equipped with a gas-introducing port, thermometer and stirrer followed by the introduction of air or oxygen with pressures as listed below. The time at which the inside temperature reached 30°C. was regarded as the reaction starting point, and the reaction was continued maintaining this temperature. Analyses of the reaction products showed the results as listed in Table 10.

Table 10

| Example No. | Alkali metal hydroxide (parts) | Reaction pressure (Kg/cm²G) | Time (hour) | Unreacted starting material (parts) | Object product (parts) | Conversion (%) | Selectivity (%) |
|---|---|---|---|---|---|---|---|
| 27 | KOH (1) | Air 120 | 2 | 0.612 | 0.624 | 55.0 | 74.5 |
| 28 | " | " | 15 | 0.063 | 0.497 | 95.4 | 34.3 |
| 29 | NaOH (0.7) | " | 2 | 0.791 | 0.275 | 41.9 | 43.2 |
| 30 | " | " | 4 | 0.326 | 0.666 | 76.1 | 57.6 |

EXAMPLES 31–32

8.17 Parts of 2,4,6-trimethylphenol, 6.0 parts of caustic potash, and 150 parts of water were fed to an autoclave equipped with a gas-introducing port, temperature recorder and stirrer, followed by the application of 120 Kg/cm² air or oxygen pressure. The time at which the inside temperature reached 30°C. was regarded as the reaction starting point, and the reaction was continued maintaining this temperature with violent stirring. Analyses of the reaction products showed the results as listed in Table 11 below.

Table 11

| Example No. | Reaction pressure (Kg/cm²G) | Time (hour) | Unreacted starting material (parts) | Object product (parts) | Conversion (%) | Selectivity (%) |
|---|---|---|---|---|---|---|
| 31 | Air 120 | 2 | 1.803 | 3.876 | 77.9 | 54.5 |
| 32 | Oxygen 120 | 1 | 0.765 | 4.575 | 90.6 | 55.3 |

EXAMPLES 35–47

1.36 Parts of 2,4,6-trimethylphenol, potassium compounds, and media as listed in Table 13 below, were fed to a reaction vessel equipped with a gas-introducing port, thermometer and stirrer, and were stirred violently. The gas-introducing port was then opened to introduce an oxygen gas. This moment was regarded as the reaction starting point. The reaction was continued under atmospheric pressure at room temperature. During the reaction, oxygen was absorbed in amounts as listed in Table 13. Analyses of the reaction products yielded the results as shown in Table 13.

Table 13

| Example No. | Medium (parts) | Potassium compound (parts) | Time (min.) | Amount of $O_2$ absorbed (volume parts) | Unreacted starting material (parts) | Object product (parts) | Conversion (%) | Selectivity (%) |
|---|---|---|---|---|---|---|---|---|
| 35 | Benzene (25) | Potassium butoxide (2) | 45 | 121 | 0.32 | 0.132 | 76.5 | 11.4 |
|  | " |  | 165 | 221 | 0.370 | 0.325 | 72.8 | 29.4 |
| 36 | n-Heptane(25) | " | 45 | 187.5 | 0.044 | 0.175 | 87.1 | 3.3 |
| 37 | Pyridine(25) | " | " | 148 | 0.077 | 0.457 | 66.4 | 7.7 |
| 38 | Acetonitrile | " | " | 122 | 0.051 | 0.416 | 69.4 | 4.9 |
| 39 | Ethyl ether | " | " | 106 | 0.014 | 0.212 | 84.4 | 1.1 |
| 40 | Hexamethyl phosphoramide | " | " | 119 | 0.011 | 0.201 | 84.0 | 1.0 |
| 41 | Dioxane | Caustic soda (1) | 190 | 241 | 0.305 | 0.793 | 41.8 | 48. |
| 42 | Benzonitrile | " | 160 | 245 | 0.343 | 0.561 | 58.8 | 38.3 |
| 43 | Toluene | " | 180 | 150 | 0.135 | 0.845 | 37.9 | 23.4 |
| 44 | m-Xylene | " | 200 | 107.5 | 0.092 | 0.972 | 28.6 | 21.0 |
| 45 | NN-dimethyl aniline | " | 240 | 158 | 0.160 | 0.897 | 34.1 | 30.8 |
| 46 | Glyme | " | 340 | 211 | 0.202 | 0.771 | 43.4 | 30.5 |
| 47 | Triglyme | " | 200 | 210 | 0.086 | 0.878 | 35.5 | 15.9 |

EXAMPLES 33–34

1.36 Parts of 2,4,6-trimethylphenol, phenolates as listed in Table 12 below, and 25 parts by volume of benzene were fed to a reaction vessel equipped with a gas-introducing port, thermometer and stirrer, and were stirred violently. Then the gas-introducing port was opened to introduce an oxygen gas. This moment was regarded as the reaction starting point. The reaction was continued under nearly atmospheric pressure at nearly room temperature. Analyses of the reaction products showed the results as listed in Table 12.

EXAMPLES 48–52

1.36 Parts of 2,4,6-trimethylphenol, 1.0 part of caustic potash, and media as shown in Table 14 below were fed to a autoclave equipped with a gas-introducing port, thermometer and stirrer under air or oxygen pressure as shown in Table 14 below. The reaction was carried out at temperatures and for periods of time shown in Table 14. Analyses of the reaction products showed the results as listed in Table 14.

Table 12

| Example No. | Phenolate (parts) | Reaction time (min.) | Amount of $O_2$ absorbed (volume parts) | Unreacted starting material (parts) | Object product (parts) | Conversion (%) | Selectivity (%) |
|---|---|---|---|---|---|---|---|
| 33 | Potassium-2,4,6-trimethyl phenolate (3.44) | 140 | 227 | 0.176 | 2.35 | 86.3 | 5.8 |
| 34 | Sodium-2,4,6-trimethyl phenolate (3.15) | 90 | — | 0.0014 | 1.85 | 68.0 | 0.05 |

Table 14

| Example No. | Medium (parts) | Temp. (°C) | Pressure (Kg/cm²G) | Time | Unreacted starting material (parts) | Object product (parts) | Conversion (%) | Selectivity (%) |
|---|---|---|---|---|---|---|---|---|
| 48 | Dimethyl formamide (25) | 30 | Air 115 | 3 hr | 0.029 | 0.563 | 97.9 | 37.8 |
| 49 | Methanol (25) | 30 | Air 118 | 2 hr | 1.120 | 0.168 | 17.7 | 62.2 |
| 50 | Dioxane (50) | Room temp. | Oxygen 5 | 80 min | 0.509 | 0.385 | 62.6 | 40.4 |
| 51 | Diglyme | Room temp. | Oxygen atmospheric pressure | 7 hr | 0.889 | 0.162 | 34.6 | 30.9 |
| 52 | Tetramethylurea (25) | Room. temp. | Oxygen atmospheric pressure | 1 hr | 0.539 | 0.160 | 60.4 | 17.4 |

EXAMPLES 53–65

1.36 Parts of 2,4,6-trimethylphenol, 1.0 part of potassium hydroxide, 25 parts of benzene, and media as shown in Table 15 below were fed to the reaction vessel equipped with a gas-introducing port, thermometer, and stirrer, and were stirred violently. Then the gas-introducing port was opened to introduce an oxygen-containing gas. This moment was regarded as the reaction starting point. The reaction was continued under nearly atmospheric pressure maintaining a reaction temperature of 30°C. During the reaction, oxygen was absorbed in amounts as listed in Table 15. Analyses of the reaction products showed the results as shown in Table 15.

Table 15

| Example No. | Medium mixed into benzene (parts) | Time (min.) | Amount of O₂ absorbed (volume parts) | Unreacted starting material (parts) | Object product (parts) | Conversion (%) | Selectivity (%) |
|---|---|---|---|---|---|---|---|
| 53 | Dimethyl formamide (6.5) | 300 | 188 | 0.540 | 0.321 | 60.3 | 34.0 |
| 54 | Tetrahydrofuran (2.6) | 410 | 215 | 0.784 | 0.190 | 42.4 | 29.5 |
| 55 | Sulfolane (4.3) | 250 | 238 | 0.662 | 0.297 | 51.4 | 37.9 |
| 56 | Acetone (2.1) | 160 | 244 | 0.738 | 0.242 | 45.8 | 34.7 |
| 57 | Pyridine (2.85) | 150 | 240 | 0.647 | 0.285 | 52.4 | 35.7 |
| 58 | Dimethylsulfoxide (2.8) | 230 | 94 | 1.127 | 0.109 | 17.2 | 41.7 |
| 59 | Hexamethyl phosphoramide (1.6) | 210 | 240 | 0.448 | 0.319 | 67.1 | 31.3 |
| 60 | Hexamethyl phosphoramide (3.2) | 270 | 241 | 0.756 | 0.362 | 44.5 | 53.5 |
| 61 | Hexamethyl phosphoramide (6.5) | 300 | 188 | 0.540 | 0.312 | 60.3 | 34.0 |
| 62 | ter-Butanol (0.67) | 180 | 242 | 0.127 | 0.131 | 90.7 | 9.5 |
| 63 | ter-Butanol (1.40) | 150 | 241 | 0.462 | 0.211 | 66.1 | 21.0 |
| 64 | ter-Butanol (2.67) | 240 | 244 | 0.587 | 0.238 | 56.9 | 27.6 |
| 65 | ter-Butanol (6.7) | 160 | 94 | 1.086 | 0.089 | 20.2 | 29.1 |

EXAMPLES 66–72

1.36 Parts of 2,4,6-trimethylphenol, 1.0 part of caustic potash, 25 parts of benzene and media as shown in Table 16 were fed to the autoclave equipped with a gas-introducing port, thermometer and stirrer, and were reacted under the conditions as listed in Table below. Analyses of the reaction products showed the results as listed in Table 16 below.

Table 16

| Example No. | Medium mixed into benzene (parts) | Time (hour) | Reaction pressure (Kg/cm²G) | Unreacted starting material (parts) | Object product (parts) | Conversion (%) | Selectivity (%) |
|---|---|---|---|---|---|---|---|
| 66 | Methanol (2.9) | 2 | Air 115 | 0.332 | 0.608 | 75.6 | 52.9 |
| 67 | Dimethyl formamide (6.6) | 16 | ″ 130 | 0.109 | 0.854 | 91.9 | 61.0 |
| 68 | Dimethyl formamide (1.3) | 13 | ″ 115 | 0.159 | 0.697 | 88.3 | 51.9 |
| 69 | Dimethyl sulfoxide (1.4) | 3 | ″ 115 | 0.139 | 0.620 | 89.8 | 45.4 |
| 70 | Water | 16 | ″ 120 | 0.233 | 0.690 | 82.9 | 54.7 |

Table 16-continued

| Example No. | Medium mixed into benzene (parts) | Time (hour) | Reaction pressure (Kg/cm²G) | Unreacted starting material (parts) | Object product (parts) | Conversion (%) | Selectivity (%) |
|---|---|---|---|---|---|---|---|
| 71 | Sulfolane (1.6) (2.2) | 3 | " 110 | 0.199 | 0.562 | 85.4 | 43.3 |
| 72 | Tetramethylurea (2.1) | 3 | " 115 | 0.204 | 0.594 | 85.0 | 45.9 |

Table 18

| Example No. | Temp. (°C.) | Pressure (Kg/cm²G) | Time (hour) | Unreacted starting material (parts) | Object product (parts) | Conversion (%) | Selectivity (%) |
|---|---|---|---|---|---|---|---|
| 81* | 80 | Air:0 $O_2$:0.2 | 6 | 1.51 | 0.09 | 24.5 | 16.4 |
| 82* | 80 | Air:5 $O_2$:1.2 | 6 | 0.891 | 0.196 | 55.4 | 15.8 |
| 83 | 30 | $O_2$:20 | 2 | 22.299 | 14.901 | 50.45 | 58.73 |
| 84 | 30 | $O_2$:50 | 2 | 10.912 | 25.166 | 75.8 | 66.0 |
| 85 | 30 | $O_2$:70 | 2 | 6.631 | 28.61 | 85.3 | 66.7 |
| 86 | 30 | $O_2$:100 | 2 | 5.069 | 31.251 | 88.3 | 70.0 |

EXAMPLES 73–80

45 Parts of 2,4,6-trimethylphenol, 150 parts of water, and 10 parts of sodium hydroxide were fed to a stainless steel autoclave equipped with a gas-introducing port, temperature recorder, and stirrer, under an oxygen pressure of 100 Kg/cm²G. The reaction was conducted at temperatures and for periods of time as shown in Table 17 below. Analyses of the reaction products showed the results as listed in Table 17.

Table 17

| Example No. | Temp. (°C.) | Pressure (Kg/cm²G) | Time (hour) | Unreacted starting material (parts) | Object product (parts) | Conversion (%) | Selectivity (%) |
|---|---|---|---|---|---|---|---|
| 73* | −10 | Oxygen 100 | 4 | 11.215 | 0.651 | 25.2 | 15.4 |
| 74 | 5 | " | 2 | 28.854 | 12.631 | 37.21 | 67.51 |
| 75 | 10 | " | " | 26.004 | 14.879 | 42.21 | 70.10 |
| 76 | 20 | " | " | 11.460 | 28.226 | 74.53 | 75.32 |
| 77 | 30 | " | " | 4.803 | 30.514 | 89.33 | 67.93 |
| 78 | 60 | " | " | 5.09 | 30.26 | 89 | 68 |
| 79 | 100 | " | " | 2.373 | 27.309 | 95 | 58 |
| 80 | 150 | " | 0.5 | 0.121 | 20.318 | 99.7 | 40.5 |

*:In Example 73, 15 parts of the starting material and 3.3 parts of NaOH were used, and 20 parts of sodium chloride (NaCl) was added to 80 parts of water.

EXAMPLES 81–86

The reaction was conducted in the same manner as in Examples 73–80 with the exception that the temperature, time and the oxygen partial pressure were changed as listed in Table 18. Results were as shown in Table 18.

Note: *: In Examples 81–82, the reaction was conducted by introducing 2 parts of 2,4,6-trimethylphenol, 100 parts of water and 0.45 part of caustic soda (NaOH).

EXAMPLES 87–96

The reaction was conducted in the same manner as in Examples 73–80 with the exception that the temperature, time and the amount of alkali were changed as listed in Table 19 below. Results were as shown in Table 19 below.

Table 19

| Example No. | NaOH (gr) | Temp. (°C.) | Pressure (Kg/cm²G) | Time (hour) | Unreacted starting material (parts) | Object product (parts) | Conversion (%) | Selectivity (%) |
|---|---|---|---|---|---|---|---|---|
| 87 | 4 | 30 | Oxygen 100 | 2 | 24.358 | 17.75 | 45.8 | 68.4 |
| 88 | 6 | " | " | " | 17.018 | 23.40 | 62.2 | 74.8 |
| 89 | 8 | " | " | " | 9.129 | 28.08 | 79.8 | 69.9 |
| 90 | 10 | " | " | " | 4.825 | 30.66 | 89.3 | 68.3 |
| 91 | 12 | " | " | " | 3.172 | 30.22 | 92.5 | 64.7 |
| 92 | 14 | " | " | " | 3.177 | 26.86 | 92.9 | 57.0 |
| 93 | 16 | " | " | " | 2.912 | 25.85 | 93.5 | 55.0 |
| 94 | 20 | 10 | " | 0.5 | 30.678 | 9.575 | 31.8 | 59.78 |
| 95 | " | 20 | " | " | 22.534 | 15.379 | 50.0 | 61.16 |
| 96 | " | 30 | " | " | 7.970 | 23.85 | 82.3 | 57.6 |

EXAMPLE 97

45 Parts of 2,4,6-trimethylphenol, 10 parts of sodium hydroxide, and 150 parts of water were fed to a stainless steel autoclave equipped with a gas-introducing pipe, temperature recorder and stirrer, and 100 Kg/cm²G oxygen pressure was applied. The reaction was conducted at 30°C. for 120 minutes, during which the pressure was reduced to 83 Kg/cm²G. The reaction product was recovered and extracted 2 times with 150 g of benzene with shaking. Analyses of benzene parts and water parts yielded 31.130 parts of 4-hydroxy-2,4,6-trimethyl-2,5-cyclohexadiene-1-one and 3.866 parts of unreacted 2,4,6-trimethylphenol from the benzene parts. 0.705 Parts of 4-hydroxy-2,4,6-trimethyl-2,5-cyclohexadiene-1-one and 0.090 parts of unreacted 2,4,6-trimethylphenol were also yielded from the water parts. Analyses of the results proved 91.2 % of conversion and 69.4% of selectivity. Expelling the benzene out of said benzene solution and concentrating the benzene, 34 parts of oily product was obtained. The oily product was analyzed to be composed of 92.2% of 4-hydroxy-2,4,6-trimethyl-2,5-cyclohexadiene-1-one and 9.6% of 2,4,6-trimethylphenol.

714 Parts of kerosene ether was added to and dissolved in the above 34 parts of oily product and then cooled with dry ice-methanol. The formed white crystals were filtered and 25.5 parts of faintly yellowish white crystals were obtained. A similar operation was repeated two times, and 22.6 parts of white crystalline 4-hydroxy-2,4,6-trimethyl-2,5-cyclohexadiene-1-one was obtained. Its melting point was 42.8°C. Measurements by means of infrared (I.R.) and nuclear magnetic resonance (N.M.R.) spectra showed the following results.

| I.R. $\nu_{max}^{KBr}$ | N.M.R. $\delta$ (ppm) |
|---|---|
| 3260 cm$^{-1}$ (O—H) | 6.5 (m. H at 3- and 5-positions) |
| 1670 cm$^{-1}$ (C=O) | 3.7 (w. H of —OH at 4-position) |
| 1630 cm$^{-1}$ (C=C) | 1.75 (s. CH$_3$ at 2- and 6-positions) |
|  | 1.35 (s. CH$_3$ at 4-position) |

What is claimed is:

1. A process for preparing 4-hydroxy-2,4,6-trimethyl-2,5-cyclohexadiene-1-one comprising reacting a phenol which is 2,4,6-trimethyl phenol, alkali metal 2,4,6-trimethyl phenolate, or alkaline earth metal 2,4,6-trimethyl phenolate, with molecular oxygen or a molecular oxygen-containing gas at an oxygen partial pressure of at least .1 Kg/cm² and at a temperature of from −20° to +200°C., and optionally in the presence of an inert liquid reaction medium having a pH of at least 5 selected from one of the group consisting of water, an inert organic liquid, or a mixture thereof, in the absence of a catalyst or in the presence of a catalyst selected from the group consisting of cobalt complexes represented by the following formulas (a), (b) and (c)

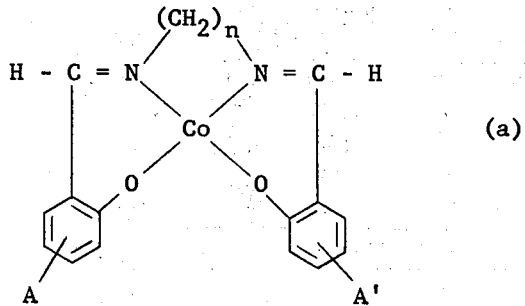

(a)

wherein, $n$ is an integer of 2–10, A and A' are hydrogen, —NO$_2$, fluoro, or —OC$_2$H$_5$,

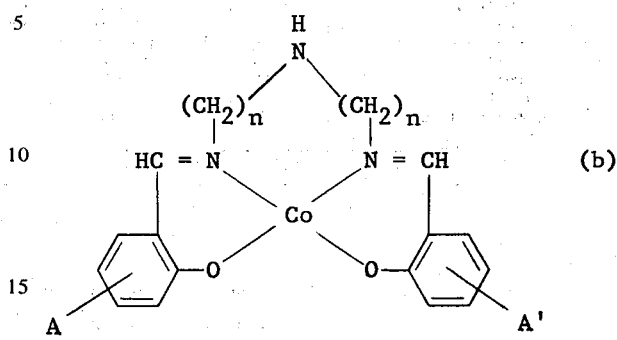

(b)

wherein $n$, A, and A' are as defined above, and

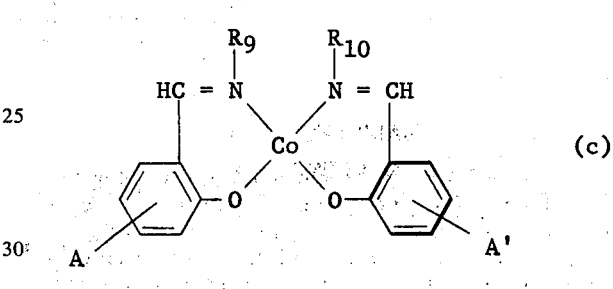

(c)

wherein, R$_9$ and R$_{10}$ are hydrogen, phenyl, alkyl, —OH, hydroxyalkyl, or benzyl, A and A' are as defined above; cobalt-di(salycylal) ethylenediimine-pyridine; cobalt-phthalocyanine; or cobalt-acetylacetone.

2. A process according to claim 1 in which the phenol is an alkali metal 2,4,6-trimethyl phenolate.

3. A process according to claim 1 in which the phenol is an alkaline earth metal 2,4,6-trimethyl phenolate.

4. A process according to claim 1 in which the phenol is 2,4,6-trimethyl phenol.

5. A process according to claim 1 in which the catalyst is: cobalt-di(salycylal)ethylenediimine-pyridine; cobalt-phthalocyanine; or cobalt-acetylacetone.

6. A process according to claim 1 wherein 2,4,6-trimethylphenol is contacted with molecular oxygen or a molecular oxygen-containing gas under the oxygen partial pressure of at least 0.5 kg/cm².

7. A process according to claim 6 wherein 2,4,6-trimethylphenol is contacted with molecular oxygen or a molecular oxygen-containing gas under the oxygen partial pressure ranging from 0.2 kg/cm² to 1000 kg/cm².

8. A process according to claim 1 wherein 2,4,6-trimethylphenol is contacted with molecular oxygen or a molecular oxygen-containing gas at a temperature ranging from −10°C. to 150°C.

9. A process according to claim 8 wherein 2,4,6-trimethylphenol is contacted with molecular oxygen or a molecular oxygen-containing gas at a temperature ranging from 20° to 100°C.

10. A process according to claim 9 wherein the oxygen partial pressure is at least 40 Kg/cm².

11. A process according to claim 9 wherein the reaction pressure is less than 300 Kg/cm².

12. A process according to claim 1 wherein said reaction is carried out in the presence of a liquid medium which is selected from at least one of the group consisting of water and an organic liquid inert to the reaction.

13. A process according to claim 12 wherein the liquid medium is water.

14. A process according to claim 12 wherein the liquid medium is an inert organic liquid mixed with water.

15. A process according to claim 12 wherein said reaction is carried out in the presence of a cobalt complex selected from the group consisting of cobalt complexes represented by the following formulas (a), (b) and (c)

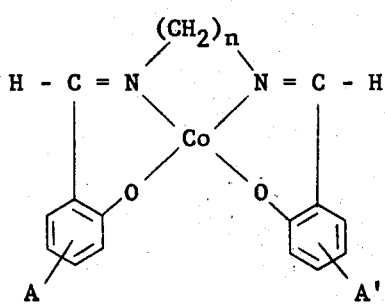

(a)

wherein, $n$ is an integer of 2–10, A and A' are hydrogen, $-NO_2$, fluoro, or $-OC_2H_5$,

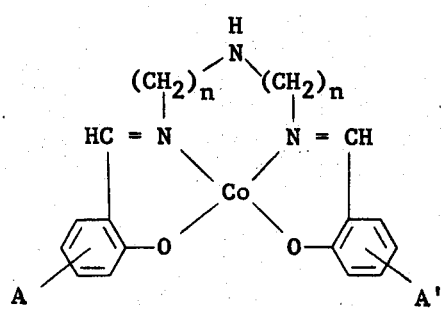

(b)

wherein $n$, A, and A' are as defined above, and

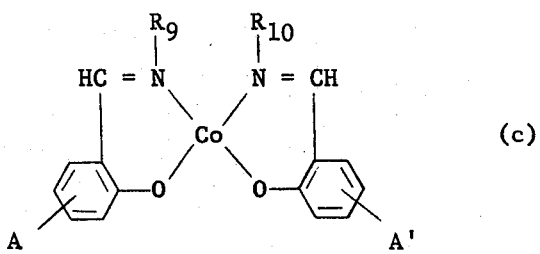

(c)

wherein, $R_9$ and $R_{10}$ are hydrogen, phenyl, alkyl, $-OH$, hydroxyalkyl, or benzyl, A and A' are as defined above.

16. A process according to claim 12 wherein said reaction is carried out in the presence of a conventional buffer or a basic reagent, added in an amount such as to adjust the pH of the reaction system to at least 5.

17. A process according to claim 12 wherein said reaction is carried out at a pH of at least 6.

18. A process according to claim 17 in which the reaction system is maintained at a pH of at least 10 until the reaction is completed.

19. A process according to claim 18 in which the reaction system is maintained at a pH of above 11 until the reaction is completed.

20. A process according to claim 17 wherein said reaction is carried out in the presence of at least one basic reagent selected from the group consisting of alkali metals, alkali earth metals and compounds thereof.

21. A process according to claim 20 in which the reaction system is maintained at a pH of from 7 to 8 by addition of at least one of alkali dihydrogenphosphate and dialkali hydrogenphosphate.

22. A process according to claim 20 wherein said basic reagent is soluble in the organic liquid medium.

* * * * *